(12) United States Patent
Benjoar et al.

(10) Patent No.: US 11,129,743 B2
(45) Date of Patent: Sep. 28, 2021

(54) SET OF NOSE-MODELLING INSTRUMENTS, PRODUCTION METHOD AND A METHOD FOR MODELLING THE NOSE

(71) Applicant: S.E.L.A.R.L DE MEDECINS PLASTICIENS PARIS, Paris (FR)

(72) Inventors: Marc David Benjoar, Paris (FR); Yaël Berdah, Paris (FR)

(73) Assignee: MCE 5 Development, Villeurbanne (FR)

( * ) Notice: Subject to any disclaimer, the term of this patent is extended or adjusted under 35 U.S.C. 154(b) by 426 days.

(21) Appl. No.: 16/076,984

(22) PCT Filed: Feb. 6, 2017

(86) PCT No.: PCT/EP2017/052551
§ 371 (c)(1),
(2) Date: Aug. 9, 2018

(87) PCT Pub. No.: WO2017/137356
PCT Pub. Date: Aug. 17, 2017

(65) Prior Publication Data
US 2019/0076288 A1  Mar. 14, 2019

(30) Foreign Application Priority Data

Feb. 9, 2016  (FR) ...................................... 1651022

(51) Int. Cl.
*A61F 5/08* (2006.01)
*B33Y 10/00* (2015.01)
(Continued)

(52) U.S. Cl.
CPC ................ *A61F 5/08* (2013.01); *B29C 64/00* (2017.08); *B33Y 10/00* (2014.12); *G16H 50/50* (2018.01);
(Continued)

(58) Field of Classification Search
CPC ........... A61F 5/08; B29C 64/00; B33Y 10/00; G16H 50/50; G05B 2219/37542;
(Continued)

(56) References Cited

U.S. PATENT DOCUMENTS 3,742,943 A  7/1973 Malmin
2001/0050689 A1* 12/2001 Park ........................ G06T 11/00
345/629
(Continued)

FOREIGN PATENT DOCUMENTS

CH  709544 A1 * 10/2015 ............... A61F 5/08
CH  709544 A1   10/2015
(Continued)

OTHER PUBLICATIONS

Written Opinion of the International Searching Authority from International Patent Application No. PCT/EP2017/052551, dated May 11, 2017.
(Continued)

*Primary Examiner* — Kandasamy Thangavelu
(74) *Attorney, Agent, or Firm* — TraskBritt

(57) ABSTRACT

An external modelling method, including applying to a nose of initial external shape $F_0$, at least two modelling instruments I, to guide the growth of the nose cartilage and thus obtain a target final external nose shape $F_f$ when the individual has stopped growing, which differs from a natural external shape $F_n$, which would be obtained naturally in the absence of intervention. A set of modelling instruments is provided, the successive shapes of which are determined to represent an evolving succession of one or more target intermediate shapes F, from the initial external nose shape $F_0$ through to the target final external shape $F_f$. A method of producing the modelling instruments is provided, during which method, starting from the initial external nose shape
(Continued)

Fi $F_0$, a target final shape $F_f$ and at least one target intermediate shape F are determined. The instruments corresponding to each target shape are manufactured.

4 Claims, 3 Drawing Sheets

(51) Int. Cl.
| | | |
|---|---|---|
| *B29C 64/00* | (2017.01) | |
| *G16H 50/50* | (2018.01) | |
| *B29L 31/00* | (2006.01) | |
| *A61B 34/10* | (2016.01) | |
| *A61B 17/00* | (2006.01) | |

(52) U.S. Cl.
CPC ............... *A61B 2017/00792* (2013.01); *A61B 2034/105* (2016.02); *A61B 2034/107* (2016.02); *A61B 2034/108* (2016.02); *B29L 2031/7532* (2013.01); *G05B 2219/34099* (2013.01); *G05B 2219/37542* (2013.01); *G05B 2219/49* (2013.01); *G05B 2219/49007* (2013.01); *G05B 2219/49008* (2013.01)

(58) Field of Classification Search
CPC ........... G05B 2219/34099; G05B 2219/49008; G05B 2219/49007; G05B 2219/49; A61B 2034/108; A61B 2034/107; A61B 2034/105; A61B 2017/00792; B29L 2031/7532; Y02A 90/10; G06T 1/00; G06T 11/00; G06K 9/00; H04N 7/18; H04N 7/15
See application file for complete search history.

(56) References Cited

U.S. PATENT DOCUMENTS

| | | | |
|---|---|---|---|
| 2006/0097422 | A1 | 5/2006 | Diamond |
| 2010/0042139 | A1* | 2/2010 | Honegger ................. A61F 5/08 606/204.45 |

FOREIGN PATENT DOCUMENTS

| | | | | | |
|---|---|---|---|---|---|
| CN | 101795400 | A | * | 8/2010 | ............... H04N 7/18 |
| CN | 102201061 | A | * | 9/2011 | ............... G06K 9/00 |
| JP | 2004046437 | A | * | 2/2004 | ............... G06T 1/00 |
| JP | 2004326179 | A | * | 11/2004 | ............... H04N 7/15 |
| WO | 2011148309 | A1 | | 12/2011 | |

OTHER PUBLICATIONS

French Search Report from French Patent Application No. 1651022, dated Oct. 5, 2016.
International Search Report from International Patent Application No. PCT/EP2017/052551, dated May 12, 2017.
European Communication pursuant to Rule 71(3) CBE for European Application No. 17706169, dated Oct. 18, 2019, 65 pages.

* cited by examiner

SET OF NOSE-MODELLING INSTRUMENTS, PRODUCTION METHOD AND A METHOD FOR MODELLING THE NOSE

TECHNICAL FIELD

The present disclosure relates to the field of medical aesthetics and more particularly the aesthetics of the nose of an individual.

The present disclosure relates to a modelling method that consists of applying to the nose, which has an initial external shape, at least two modelling instruments so as to guide the growth of cartilage or even bone of the nose and thus obtain a target final external shape of the nose when growth of the individual is complete, which is different from a natural external shape that would obtain naturally in the absence of intervention.

The present disclosure also relates to a set of modelling instruments the successive shapes of which are determined in order to represent a progressive succession of one or more target intermediate shapes from the initial external shape of the nose to the target final external shape.

It also relates to a method for producing modelling instruments during which, based on the initial external shape of the nose, a target final shape and at least one target intermediate shape are determined. Instruments are produced corresponding to each target shape.

BACKGROUND

In the field of cosmetic surgery, it is known to modify the shape of the nose of an individual with the aim of aesthetic improvement. The conventional method, the surgical operation known as rhinoplasty, is intended to remodel the nose in order to modify the external shape thereof. The nose is composed of several parts or units, which can be modified separately by reducing some and increasing others. The aim of aesthetic rhinoplasty is to obtain an improved impression of visual harmony between these different parts, in a form that will result in a natural-looking nose that does not appear to have been remodeled." In order to improve the healing process following a rhinoplasty operation, a plurality of splints is known from the document U.S. Pat. No. 3,742,943 A for placing on the nose while the swelling diminishes.

Generally, this is specifically to correct inelegances that are present, having appeared, in particular, during adolescence. Typically, the purpose of rhinoplasty operations is to reduce a bump present close to the nasal bridge ("dorsum") and visible in profile.

This operation can only be carried out when growth of the individual is complete, i.e., from about 16 years of age in women or about 19 years of age in men.

Rhinoplasty operations are carried out under general anesthesia, which is off-putting or even frightening for some patients. The cost of this operation is significant, as it amounts to several thousand euros.

In order to avoid these drawbacks, it was proposed to intervene on the external shape of the nose, while acting during growth of the face, by applying thereon one or more localized reduction devices called "nasal compression splints," which apply a force at one or specific points, generally under traction and sometimes pressure. These nasal compression splints are rigid and non-deformable. When growth of the nose makes wearing the splint painful, a new device of a slightly larger size is applied.

An orthopedic device is known from the document WO 2011/148309 A1 for conditioning the growth of the nasal pyramid during the period of growth of an individual. A spring wire is positioned on the nasal pyramid so as to exert a pressure on several points thereof. However, the wires can deform over time, which makes adjustment very difficult, or even approximate, and does not allow accurate monitoring or control of the growth of the pyramid of the nose of the individual. This method requires regular adjustment of the shape of the wire, depending on the pressure that it is desired to exert, and ongoing adjustment thereof in order to reach the target shape.

Furthermore, this method has not really been adopted by professionals.

The purpose of the present disclosure is to overcome at least one of these drawbacks. The present disclosure also seeks to improve the predictability of the results, and to reduce the discomfort undergone during aesthetic modifications to the shape of the nose.

BRIEF SUMMARY

According to a first aspect of the present disclosure, provision is made for a method for producing instruments for modelling the shape of the nose of an individual. The production method comprises the following steps:
  based on an initial shape, representing the initial shape of an external surface of a region of the nose of the individual, called modelling region, as it exists at an initial time:
  determining a target final shape, representing the shape that it is sought to obtain at a final time, for the modelling region of the nose of the individual, and determining at least one target intermediate shape, representing a shape that it is sought to obtain at an intermediate time situated between the initial time and the final time, for the modelling region of the nose of the individual, and
  producing, for each of the target shapes, at least one modelling instrument arranged in order to be applied and held in contact with the modelling region of the nose of the individual, in such a way as to form an obstacle, which will guide the growth of the cartilage or even the bone of the nose.

The modelling instrument includes a contact surface, which is in contact with the face, having a stable three-dimensional shape that represents or corresponds with the target shape in a complementary manner. According to the present disclosure, provision is thus made for a plurality of modelling instruments intended to be applied one after another on the face of the individual with a view to guiding the growth of the cartilage or even the bone of the nose.

It will be noted that in the present disclosure the cartilaginous growth is actually guided by the shape of each instrument, which constitutes a sort of stop, which the growing cartilage cannot easily pass. The shape of the nose that will be obtained is thus very close to that of the instrument, and thus be easily assessed and determined.

In the prior art, even if it were applied, a method such as that of the document WO 2011/148309 does not make it possible to propose a shape determined in advance for the final result for the shape of the nose. In addition, as the adjustments are made on the forces applied, and in addition without accurate knowledge of the intensity, it is very difficult to anticipate the result that will be obtained. In fact, by modifying the local curvature of a wire spring, i.e., by modifying only, and approximately, the force applied at several points, it is extremely difficult to know by what exact distance the growth of these several points will be slowed, and even more so for the rest of the nose.

It will be noted that the present disclosure can be implemented much more simply and with fewer precautions than a surgical operation, has fewer risks and does not require the same type of competences. On the other hand, this type of action seems quite inadequate for correcting serious or functional deformities.

According to a feature of the present disclosure, a mold or a 3D printer is used in order to produce at least the contact surface of at least one of the instruments. In a preferred embodiment, a mold or a 3D printer is used in order to produce the contact surface of each of the instruments. Moreover, the instrument or instruments can be produced entirely by molding or by a 3D printer. These methods have the advantage of being simple and cost-effective.

Preferably, the instrument has a stable form, i.e., such that the instrument is rigid with respect to the ability of flesh to deform. Typically, the rigidity and/or the force applied are determined so as not to deform the existing cartilage. Typically, this rigidity is obtained with a high elasticity chosen in order to sufficiently retain its geometrical contact shape and to impose this geometrical contact shape in a distributed and permanent manner, producing a molding effect on a biological substance pressing against the instrument; cartilage herein. That is to say that the application of the instrument will produce a pressure force at the point where it is in contact with the face, and leave a free space or one with lower pressure at the point where the shape of the instrument is set back with respect to the current shape of the face when free. Typically, the action takes place by guiding the cartilaginous growth towards the free spaces or those with lower pressure, and not by deformation of the existing cartilage.

Preferentially, in ways that may be combined together, the method provides for:
  recording the current external shape of the modelling region of the nose of the individual, thus providing the initial shape,
  extrapolating the growth of the nose, based on the recorded initial shape, in order to elaborate a final shape, called natural final shape, representing the shape that will be adopted by the modelling region at the final time in the absence of intervention, and
  determining the target final shape, based on the natural final shape and possibly also of the initial shape.

The method has the advantage of adapting to each individual and to provide from the start the possible target future shape or shapes, depending on the intrinsic parameters of the individual. In addition, it is possible to provide for the different target intermediate shapes between the initial shape and the target final shape, and thus to provide in advance for producing the modelling instruments. It is thus possible to improve the predictability of the shape of the nose.

According to a feature, the method provides for recording the external shape of the modelling region of the nose at an intermediate time. This makes it possible optionally to correct predictions of the different target intermediate shapes depending on the progress of the cartilaginous growth of the nose of the individual, in order to obtain the target final shape.

The method provides for several methods for recording the initial shape of the nose. It is possible to record the initial shape of the nose by photography (for example, 3D), by radiography or by molding in order to obtain an imprint of the shape of the nose. It is also possible to envisage using a combination of some or all of these methods for obtaining the imprint of the shape of the nose.

Preferably, the step of extrapolation and/or determination of the target final shape comprises modifying a computerized three-dimensional image. This modification of a three-dimensional image can be carried out manually or in an automated manner. This characteristic makes it possible to visualize the modifications of the shape of the nose and allows the target intermediate shapes and the target final shape to be defined.

According to a second aspect of the present disclosure, in particular, according to the first aspect, a method for aesthetic modelling of the external shape of the nose of an individual is proposed, by applying on the face, and more particularly on the external surface of the nose, a modelling instrument including a contact surface having a stable determined shape depending on a target future external shape for the nose.

The method comprises producing a plurality of modelling instruments, the successive shapes of which are determined in order to represent a progressive succession of one or more target intermediate shapes from the initial external shape of the nose as recorded in the current state at the initial time up to the target final external shape of the nose. According to the present disclosure, the method comprises applying the instruments on the face of an individual who is still growing, i.e., an individual whose nose cartilage is still growing. The individual is, for example, a child or preferably an adolescent. The initial time corresponds to a time sufficiently early as to be able to act on the cartilaginous growth. Preferably, the initial time corresponds approximately to the start of adolescence. The final time corresponds, for example, to the end of adolescence. Between the initial time and the final time, the application of the modelling instruments takes place regularly for extended periods, for example, several hours per day, in particular, at night, or per week, successively over time and as the individual grows. The modelling instruments have different shapes with respect to one another and are applied on the face of the individual one after another in a predetermined order. Each instrument is applied on the nose of the individual for several hours per day or per week; each instrument being able to be used for several weeks or several months. This time is, for example, the time necessary in order to obtain the target intermediate shape corresponding to the instrument, before continuing the modelling method with a following instrument. The intermediate shape is, for example, a shape close, or identical, to that of the current instrument, or a shape for which it is considered that keeping the current instrument would not result in any further improvement, or a compromise between the two. The modelling method thus makes it possible to guide the cartilaginous growth of the modelling region of the nose until the target final shape is obtained, or a shape that is progressively becoming closer thereto by means of the successive application of the modelling instruments. Preferably, the modelling of the nose is carried out by guiding the cartilaginous growth towards the one or several target intermediate shapes. However, it is not obligatory to pass through all of the target intermediate shapes. Thus, a shape becoming closer to the target final shape of the nose can be an intermediate shape between the final shape called natural final shape and the target final shape.

The cartilaginous skeleton mainly comprises the lateral cartilage, the septal cartilage and the alar cartilage. Each instrument can act on all or part of the cartilaginous skeleton so as to guide the cartilaginous growth of the modelling region of the nose.

The modelling method according to the present disclosure makes it possible on the one hand to improve the predictability of the shape of the nose obtained and on the other hand to facilitate and improve the quality of monitoring of the progress of the cartilaginous growth of the nose of the individual. In fact, once the instruments are made, it is sufficient to monitor the satisfactory progress of the cartilaginous growth and to apply the successive instruments in the predetermined order up to the final instrument.

According to a feature of the present disclosure, at least one target intermediate shape can be modified depending on the intermediate results obtained at the intermediate times. This makes it possible to adapt or correct the different target intermediate shapes of the modelling instruments depending on the progress of the cartilaginous growth of the nose of the individual, in order to obtain the target final shape, or close thereto. In some cases, this can lead to a slight modification of the target final shape of the nose.

Preferably, a siliconized or silicone interface is applied between the modelling instrument and the nose. This characteristic makes it possible to improve the comfort of application of the instrument on the nose and to facilitate the hygiene of the skin and avoid unpleasant temporary visible marks.

According to a third aspect of the present disclosure, in particular, according to the first and/or the second aspect, the present disclosure proposes a set of modelling instruments to be applied on the nose of an individual whose cartilage is growing, a child or an adolescent, in order to guide the cartilaginous growth of the nose. Each instrument has respectively an outer surface and an inner surface called contact surface coming into contact with at least one modelling region of the nose.

The set comprises at least:
  a final instrument, the contact surface of which has a shape representing or corresponding complementarily to a target final shape for the nose of the individual, and
  one or more intermediate instruments, the contact surface of which has a shape representing or corresponding complementarily to an intermediate shape between the initial shape and the target final shape for the nose of the individual.

The set of instruments according to the present disclosure makes it possible on the one hand to improve the predictability of the shape of the nose obtained and on the other hand to facilitate and improve the quality of monitoring the progress of the cartilaginous growth of the nose of the individual.

Preferably, the instruments are not adjustable, in particular, in the resting shape. Preferably, during the application of an instrument on the nose of the individual, the contact surface of the instrument with the skin of the nose corresponds to at least 50% of the skin surface of the nose. This makes it possible to facilitate and improve the stability of the instrument and thus the geometrical shapes thereof and in this way to ensure that the modelling instrument allows the target shape of the nose to be obtained.

According to a preferred embodiment, the instruments extend along the nasal bridge between the columella and the nasal root. This characteristic makes it possible to apply the instrument on all of the cartilaginous parts of the nose.

Preferably, the instruments are arranged in order to bear on the forehead of the individual. This characteristic makes it possible to position the instrument with respect to the nose. Preferentially, the instruments are arranged in order to bear on the nasal root.

Preferentially, the instruments comprise a device for positioning and holding around the cranium. According to a preferred embodiment, the positioning device has at least one elastic support on the occipital bone of the cranium. This makes it possible to hold the instrument in place with respect to the head and to provide thereto all or part of the pressure thereby applied to the nose. According to a preferred embodiment, the elastic positioning device is in the form of elastic straps or headbands.

Optionally, the instruments are produced from resin, for example, from curable synthetic or plant material.

BRIEF DESCRIPTION OF THE DRAWINGS

Other advantages and characteristics of the present disclosure will become apparent on reading the detailed description of embodiments, which are in no way limitative, and from the following attached drawings.

DETAILED DESCRIPTION

As these embodiments are in no way limitative, variants of the present disclosure can be considered comprising only a selection of the characteristics described hereinafter, in isolation from the other characteristics described (even if this selection is isolated within a sentence comprising these other characteristics), if this selection of characteristics is sufficient to confer a technical advantage or to differentiate the present disclosure with respect to the state of the prior art. This selection comprises at least one, preferably functional, characteristic without structural details, and/or with only a part of the structural details if this part alone is sufficient to confer a technical advantage or to differentiate the present disclosure with respect to the state of the prior art.

Firstly, a method for aesthetic modelling of the external shape of a nose 1 of an individual will be described with reference to FIGS. 1 to 4. According to the present disclosure, the method consists of applying on the face of a growing individual, and more particularly to the nose thereof, at least two modelling instruments $I_i$ and $I_f$ (arrow b in FIGS. 1 and 2) so as to guide the cartilaginous growth of the nose and thus to obtain a target final external shape $F_f$ of the nose, when growth of the individual is complete, called time $t_f$, which is different to a natural external shape $F_n$, which would be obtained naturally in the absence of intervention (arrow a in FIG. 1).

Figure 1:
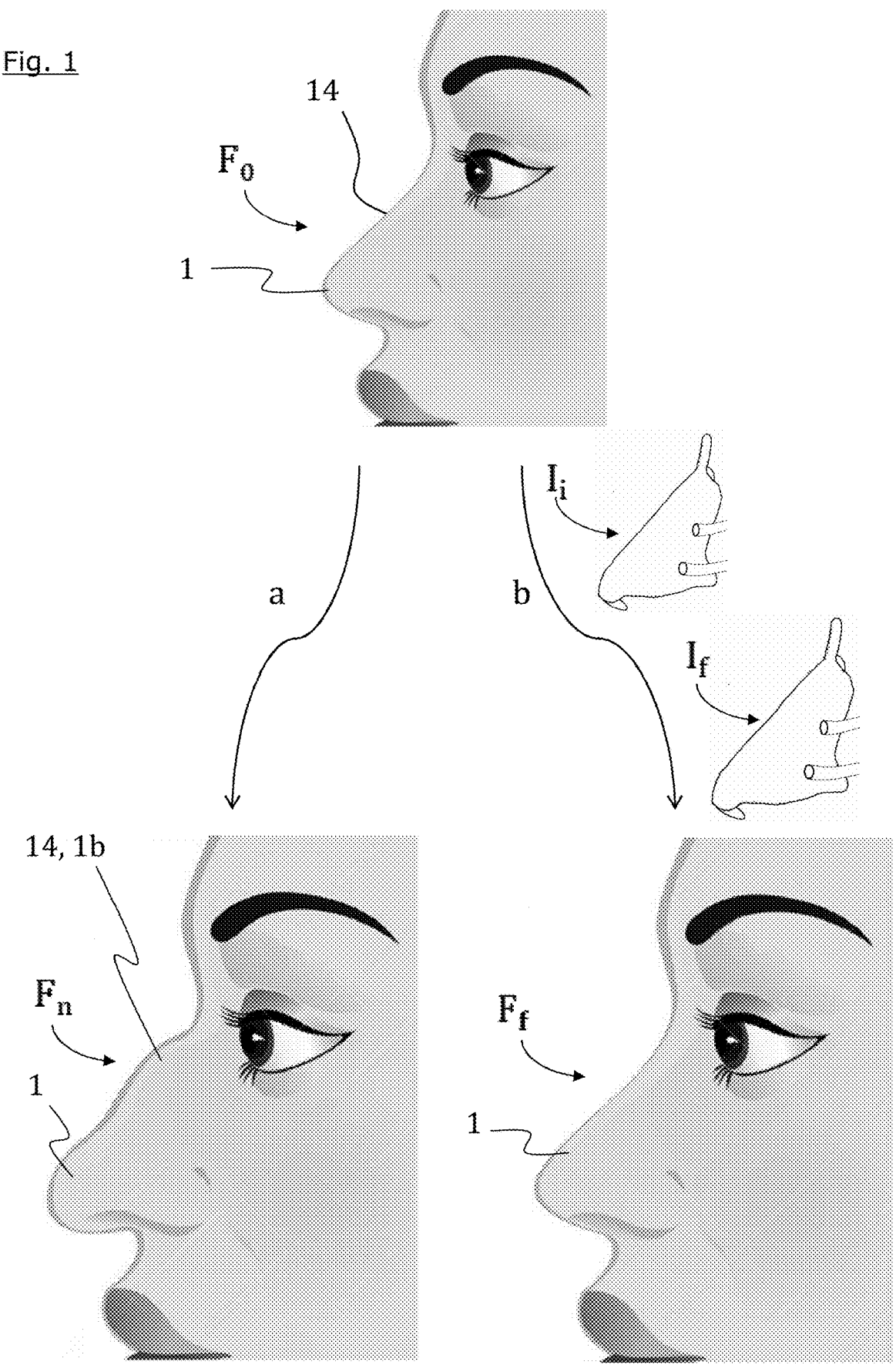
FIG. 1 illustrates a method for aesthetic modelling of the external shape of the nose, according to the present disclosure, via profile views of a face between an initial shape and a natural final shape on the one hand and a target final shape obtained by means of at least two modelling instruments on the other hand.
Figure 2:
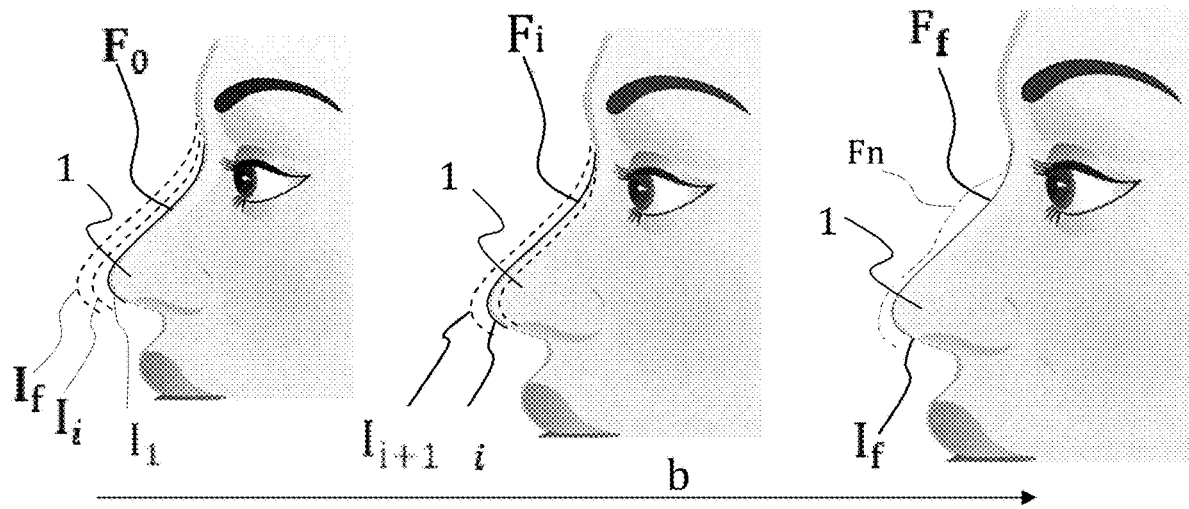
FIG. 2 corresponds to the procedure b in FIG. 1 and illustrates the effect of the application of the modelling instruments on the shape of the nose, during the growth of the individual.

The growing individual is an individual whose cartilaginous growth of the nose is ongoing, i.e., generally a child or an adolescent. With reference to FIGS. 1 and 2, during childhood or pre-adolescence, called time $t_0$, it is frequent for the nose of an individual to have an external shape, called initial shape $F_0$, giving an impression of visual harmony. However, during adolescence, the cartilaginous growth of the nose may result in a bump 1b appearing on the bridge 14 of the nose, typically due to excessive growth of the lateral cartilage and/or the septal cartilage. This bump is particularly visible in profile and is definitive. Once the growth of the individual is complete, the nose has a final external shape called natural shape $F_n$, but which is no longer satisfactory with respect to the impression of visual harmony that it gives.

Figure 4:
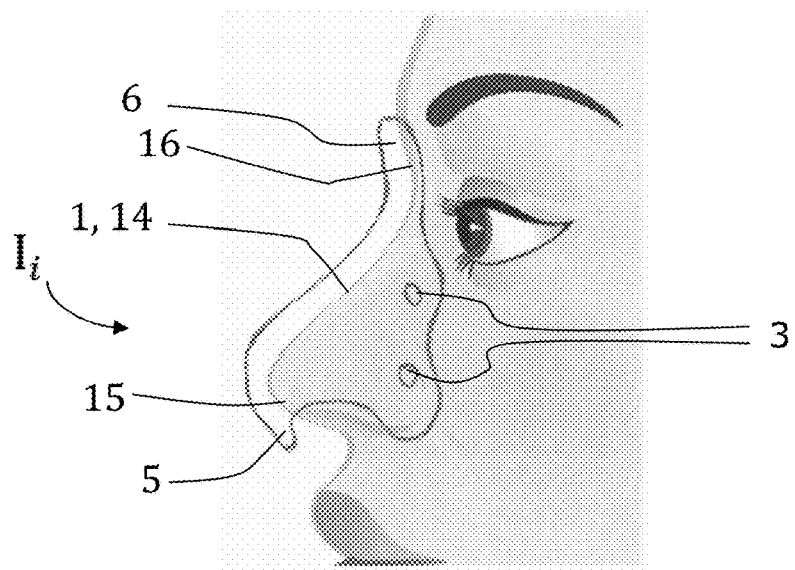
FIG. 4 is a profile view of a face, on which is placed an instrument for modelling the nose, the instrument being transparent.

By modelling instrument $I_i$ is meant an item such as a splint or a mask covering at least the external surface of a region of the nose, called "modelling region." In particular, the modelling instrument $I_i$ includes an inner contact surface $S_i$ having a stable determined shape and bears on the modelling region of the nose (FIGS. 2 and 4). FIG. 2 shows a contact line representing the progress of the contact surface during the course of the different instruments. The different contours shown correspond to the different modelling instruments ($I_1$, $I_i$, $I_{i+1}$, $I_f$) applied on the nasal bridge, the current one of which being shown by a solid line and the others by dashed lines.

Figure 5:
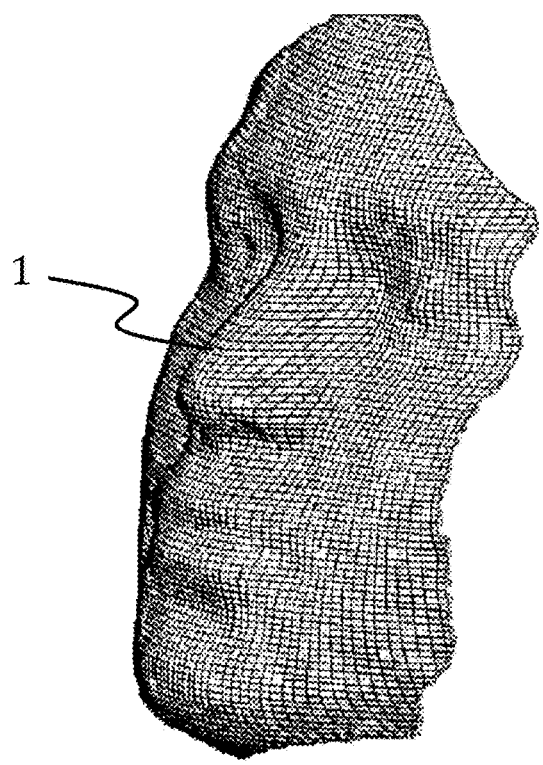
FIG. 5 is a computerized three-dimensional image of a face showing, in particular, the nose in its initial shape.

Before applying the modelling instruments $I_i$, the modelling method provides, at the time $t_0$, for recording the current external shape of the modelling region of the nose of the individual, so as to obtain the initial shape $F_0$ of the nose (FIG. 1), for example, according to known methods (see FIG. 5, described below). Then, from this initial shape $F_0$, the cartilaginous growth of the nose is extrapolated, in order to elaborate the final shape, called natural final shape $F_n$, representing the shape that the modelling region of the nose will adopt in the absence of intervention. The target future shape $F_f$ is determined depending on the final shape, called natural shape $F_n$, the initial shape $F_0$ and the subjective assessment of the individual who wishes to improve the appearance of the external shape of the nose. Preferably, the target final shape of the nose is determined so as to find a compromise between the expected final shape, called natural shape, and the final shape desired by the individual, so that the target final shape can more easily be achieved. Moreover, at least one target intermediate external shape $F_i$ is determined, representing a shape that it is sought to obtain (or at least come close to, or progress towards) at an intermediate time $t_i$ situated between the initial time $t_0$ and the final time $t_f$. This makes it possible to progressively model the nasal region. Finally, the intermediate modelling instruments $I_i$ and the final modelling instrument $I_f$ are produced, each including an inner contact surface $S_i$ or $S_f$ corresponding complementarily to the intermediate shapes $F_i$ or the target future shape $F_f$. The modelling instruments can be produced simultaneously, or as the growth of the individual progresses.

According to the present disclosure, the modelling method provides for at least one intermediate modelling instrument $I_i$ and one final modelling instrument $I_f$. Each of the intermediate modelling instruments $I_i$ includes a contact surface $S_i$ having a stable determined shape depending on the target future external shape $F_f$ giving the impression of visual harmony so as to avoid the final external shape called natural shape $F_n$ when growth of the individual is complete. The final modelling instrument $I_f$ includes a contact surface $S_f$ corresponding to the target future external shape $F_f$.

According to the present disclosure, and with reference to FIG. 2, a succession of modelling instruments $I_i$ is applied, the successive shapes of which are determined in order to represent a progressive succession of one or more target intermediate shapes $F_i$ from the initial external shape $F_0$ of the nose as recorded in a current state (during childhood or adolescence) at the initial time $t_0$ and up to the target final external shape $F_f$ of the nose when growth is complete. The succession of instruments makes it possible to progressively guide the cartilaginous growth of the nose. FIG. 2 shows, in particular, the view on the left, a superimposition of contact lines corresponding to the modelling instruments, in particular, the modelling instrument $I_1$ at the start of the modelling process, then above an intermediate modelling instrument $I_i$ and again above a final modelling instrument $I_f$ corresponding to the last instrument applied in order to obtain the target final shape $F_f$, showing different modelling instruments that will be applied on the modelling region of the nose. Clearly, the number of successive instruments may vary, for example, depending on the individuals or the procedures utilized.

With reference to FIGS. 2 and 4, the modelling instruments $I_i$ must be applied regularly to the face of the individual during the course of growth and for extended periods, as for orthodontic devices. It is preferable to apply the instruments for several hours per day, in particular, at night, or per week, so as to form an obstacle to the cartilaginous growth of the nose and thus to guide it. Each modelling instrument $I_i$ constitutes a sort of stop, which the growing cartilage cannot easily pass. FIG. 2, in particular, the middle view, shows the effect, viewed in profile, of the intermediate instruments $I_i$ and $I_{i+1}$ on the bridge 14 of the nose. The shape of the nose that will be obtained is thus very close to that of the instrument, and thus can easily be assessed and determined. Of course, the purpose of the modelling instrument is not to prevent cartilaginous growth, but to guide it in the shape of the instrument. Once the intermediate shape $F_i$ of the nose is obtained, or close thereto, the following modelling instrument $I_{i+1}$ is applied and so on (suggested by the dashed line in FIG. 2). The modelling instruments $I_i$ are applied successively over time, for example, every three months, and as the individual grows, thus making it possible to guide the cartilaginous growth of the modelling region of the nose until the target final shape $F_f$ is obtained, or close thereto, by means of the last modelling instrument $I_f$. The modelling method does not envisage a limited number of intermediate instruments.

So as to make the application of the instrument more comfortable and to avoid difficulties with skin hygiene, a siliconized interface is applied between the modelling instrument and the nose.

Depending on the intermediate results obtained at the intermediate times, for example, in the case of a mismatch between the target intermediate shapes of the instruments and the actual external shape of the nose, it is possible to modify the future target final external shape and/or the target intermediate shapes. New intermediate modelling instruments can then be produced, replacing the intermediate instruments initially provided.

With reference to FIGS. 2 to 4, a set of modelling instruments will now be described, to be applied on the nose 1 of an individual whose cartilage is growing, in order to guide the cartilaginous growth of the nose. Each modelling instrument $I_i$ has an outer surface $S_e$ and an inner surface called contact surface $S_i$ coming into contact with at least one modelling region of the nose. As described above, the set of instruments comprises:
- a final instrument $I_f$, the contact surface of which has a shape representing or corresponding complementarily to a target final shape $F_f$ for the nose of the individual, and
- one or more intermediate instruments $I_i$, the contact surface $S_i$ of which has a shape representing or corresponding complementarily to an intermediate shape $F_i$ between the initial shape $F_0$ and the target final shape $F_f$ for the nose 1 of the individual (FIG. 2).

The modelling instruments $I_i$, $I_f$ differ from one another at least by an inner contact surface having a different shape in order to allow a determined shape to be given to the nose after successive application of the different instruments over time and as the individual grows. FIG. 2 shows, in particular, a contact line corresponding to each modelling instrument ($I_1$, $I_i$, $I_{i+1}$, $I_f$) applied on the nasal bridge.

Figure 3A:
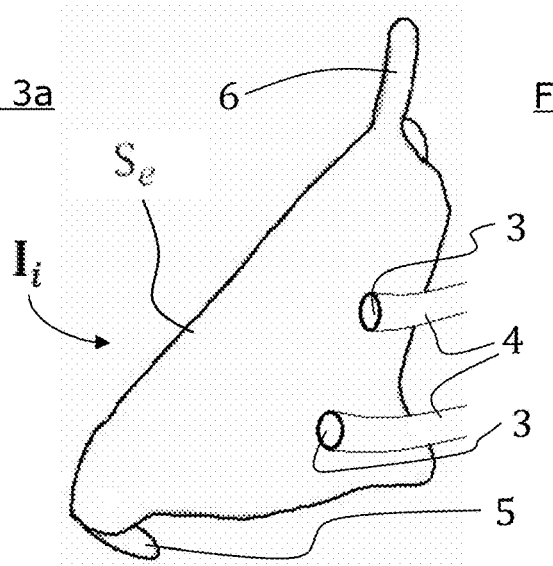
FIG. 3a is a right side view of a modelling instrument, according to the present disclosure.
Figure 3B:
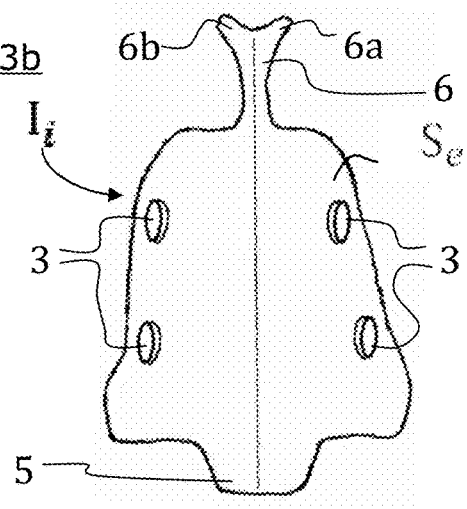
FIG. 3b is a front view of a modelling instrument, according to the present disclosure.

With reference to FIGS. 3a, 3b and 4, the modelling instruments $I_i$ extend along the nasal bridge between the nasal columella 15 and the nasal root 16, so that they can be placed on the external surface of the nose, and more particularly above the cartilaginous parts of the nose. For example, the instrument can bear on the nasal bridge 14, and on the nasal columella 15 by one end 5 of the instrument, making it possible to exert an upward restraint.

Moreover, the instrument includes an upper end 6 for bearing on the forehead of the individual and making it possible to position the modelling instrument with respect to the nose, but without acting on the bony face. Preferentially, with reference to FIG. 3b, the upper end 6 comprises two lobes 6a, 6b provided in order to bear on either side of the nasal bone.

Preferably, the modelling instrument comprises an elastic positioning device 4 around the cranium that bears on the occipital bone of the cranium in order to hold the modelling instrument $I_i$ with sufficient pressure on the nose of the individual so that the instrument forms a stop for the cartilaginous growth. With reference to FIG. 3a, the elastic positioning device 4 has elastic straps or elastic headbands that are fixed to the outer surface $S_e$ of the modelling instrument and encircle the cranium of the individual. According to a particular embodiment (not shown), the instrument comprises an occipital cleat arranged to be placed by its structural form close to the occiput of the cranium and allowing the elastic straps to be passed through the cleat.

With reference to FIGS. 3a, 3b and 4, the modelling instruments comprise fastening systems 3 on the outer surface $S_e$ of the instrument for attaching the elastic positioning device. According to a first example embodiment, the fastening systems 3 comprise cylindrical studs around which the elastic headbands can be attached. According to a second example embodiment, the cover of the instrument has holes for attaching the elastic headbands thereto.

Figure 6:
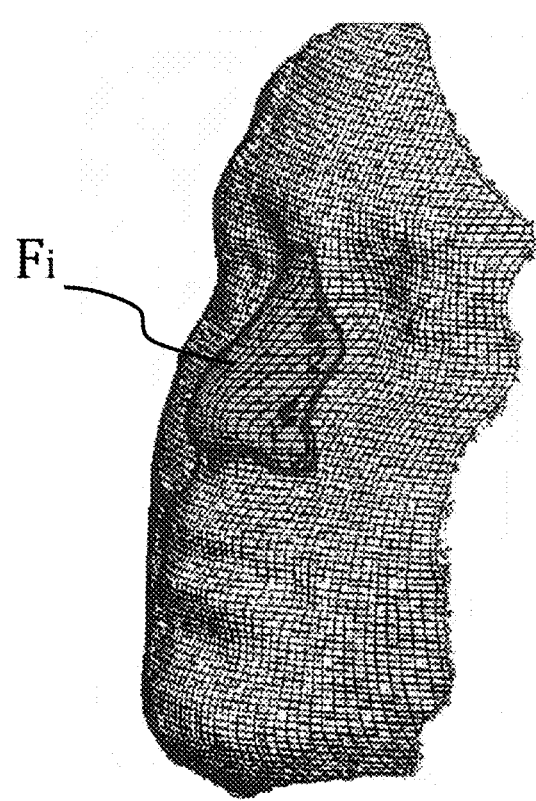
FIG. 6 is a computerized three-dimensional image of the face shown in FIG. 5 showing the nose in an intermediate shape.

A method for producing modelling instruments for shaping the nose 1 of an individual will now be described with reference to FIGS. 5 and 6. As described above with the modelling method, it is necessary to apply at least one intermediate modelling instrument $I_i$ in order to model the region of the nose undergoing cartilaginous growth so as to obtain target intermediate shapes $F_i$ and a final modelling instrument $I_f$ a short time before growth is complete or on completion of growth, in order to obtain the final external shape $F_f$ of the nose. Firstly, with reference to FIG. 5, it is necessary to record the current external shape of the modelling region of the nose 1 of the individual at a time called initial time $t_0$ so as to obtain the initial shape $F_0$. Several methods are possible to record the initial shape $F_0$ of the nose. For example, the face is photographed using the method called "3D photography." 3D radiography can also be used. Provision is also made to mold the face so as to obtain a physical imprint. Finally, provision is made to use a combination of some or all of these methods. According to a preferred embodiment, the face of the individual and more particularly the initial shape of the nose are digitized so as to obtain a computerized three-dimensional image of the nose that can be viewed on a computer (FIG. 5). A method is known, for example, from the document US 2006/0097422 A1 making it possible to obtain a three-dimensional image of a surface of a part of a body, and to manipulate the image so as to obtain a desired shape or profile.

For example, in a similar way to document US 2006/0097422 A1, based on the computerized image of the initial shape of the nose, this image is manipulated in order to extrapolate the cartilaginous growth of the nose, by means of image processing software. The initial three-dimensional image is modified so as to obtain a three-dimensional image of the final shape, called natural shape. It is thus possible to show the progress of the growth of the nose and the final shape, called natural shape $F_n$, representing the shape that the nose or the modelling region of the nose would adopt when growth is complete in the absence of intervention.

Depending on the initial shape and the assessed natural final shape, the target final shape $F_f$ is extrapolated or determined using image processing software, by modifying the initial computerized three-dimensional image manually or in an automated manner. Once the target final shape is defined, at least one intermediate shape $F_i$ of the nose is determined by computerized means, representing a shape that it is sought to obtain at an intermediate time situated between the initial time and the final time so as to progressively guide the cartilaginous growth of the nose between the initial shape and the target final shape. FIG. 6 shows an example of an intermediate shape of the nose. The surface shown in grey is the external surface of the nose and corresponds to a target intermediate shape $F_i$, which it is sought to obtain at an intermediate time. Determining this surface also makes it possible to define the inner surface called contact surface $S_i$ of the modelling instrument, as the contact surface of the intermediate instrument is complementary to the external surface of the nose at the intermediate time in question.

For each of the target shapes, at least one modelling instrument $I_i$ is produced, arranged in order to be applied and held in contact with the modelling region of the nose of the individual, so as to guide the cartilaginous growth of the nose of the individual. The modelling instruments $I_i$ are produced such that they include a contact surface $S_i$ having a stable shape, i.e., they have sufficient rigidity so that each instrument represents or corresponds to the target shape complementarily, and keeps this shape sufficiently well once applied, in order to act on the nose.

Provision can thus be made for as many modelling instruments as necessary, in order to apply them one after another on the face of the individual with a view to guiding the cartilaginous growth of the nose.

Of course, the invention is not limited to the examples which have just been described and numerous adjustments can be made to these examples without exceeding the scope of the claimed invention.

The invention claimed is:

1. A method for producing instruments for modelling a shape of a nose of an individual, said method comprising:

selecting a region of the nose of said individual as modelling region;

recording current external shape of the modelling region of the nose of the individual as an initial shape, $F_o$ of the external surface at an initial time, $t_o$;

based on said initial shape, $F_o$, extrapolating growth of the nose in order to arrive at a final natural shape, $F_n$, representing a shape that will be adopted by the modelling region at a final time, $t_f$ in the absence of intervention;

determining based on said final natural shape, $F_n$ and said initial shape, $F_o$, a final target shape, $F_f$ representing a shape that is sought to be obtained at the final time, $t_f$, for said modelling region of the nose of said individual;

determining at least one intermediate target shape, $F_i$, representing a shape that is sought to be obtained at an intermediate time, $t_i$ situated between the initial time, $t_o$ and the final time, $t_f$, for said modelling region of the nose of said individual; and producing, for each of said intermediate target shapes, $F_i$ and the final target shape, $F_f$ at least one modelling instrument, $I_i$ arranged in order to be applied and held in contact with the modelling region of the nose of said individual, in such a way as to form an obstacle to the cartilaginous growth of the nose of said individual;

wherein said modelling instrument includes a contact surface, $S_i$ having a stable shape that represents or corresponds complementarily to said each of said intermediate target shapes, $F_i$ and the final target shape, $F_f$, thus forming a plurality of modelling instruments provided in order to be applied one after another on the face of said individual with a view to guiding the cartilaginous growth of their nose.

2. The method for producing instruments according to claim 1, further comprising using a mold or a 3D printer in order to produce at least the contact surface, $S_i$ of at least one of said instruments, $I_i$.

3. The method for producing instruments according to claim 1, further comprising recording the initial shape of the nose by photography or 3D photography or radiography or 3D radiography or by molding or a combination of all or some of these methods.

4. The method for producing instruments according to claim 1, characterized in that the step of extrapolation and/or determination of the final target shape, $F_f$ comprises modifying a computerized three-dimensional image of the nose of said individual.

* * * * *